United States Patent [19]

Whiteside

[11] Patent Number: 5,022,390
[45] Date of Patent: Jun. 11, 1991

[54] ORTHOTIC DEVICE FOR LIMITING LIMB NOTION AT A JOINT

[76] Inventor: Stacey A. Whiteside, 6810 S. Carney Ave., Tempe, Ariz. 85283

[21] Appl. No.: 522,314

[22] Filed: May 11, 1990

[51] Int. Cl.⁵ .............................................. A61F 5/00
[52] U.S. Cl. ................................ 128/80 H; 128/80 R
[58] Field of Search ..................... 128/68, 69, 75, 77, 128/80 R, 80 C, 80 F, 80 H, 87 R, 88, 89 R, 90; 36/47, 125; 16/374, 376, 377; 403/77, 115, 117

[56] References Cited

U.S. PATENT DOCUMENTS

| | | | |
|---|---|---|---|
| 830,894 | 9/1906 | Garrod | 128/80 H |
| 1,232,899 | 7/1917 | De Puy | 128/89 R |
| 1,671,991 | 6/1928 | Lindner | 403/115 X |
| 1,708,757 | 4/1929 | Freileweh | 128/80 H X |
| 2,477,591 | 8/1949 | Follis | |
| 3,970,305 | 7/1976 | Hawkins | 128/87 R X |
| 4,254,953 | 3/1981 | Marchetti | 128/77 X |
| 4,320,748 | 3/1982 | Racette et al. | 128/80 R |
| 4,353,361 | 10/1982 | Foster | 128/80 F X |
| 4,494,534 | 1/1985 | Hutson | 128/80 F |
| 4,604,997 | 8/1986 | DeBastiani et al. | 128/77 X |
| 4,632,096 | 12/1986 | Harris | 128/80 F |
| 4,641,393 | 2/1987 | Lautenschlager | 403/117 X |
| 4,665,904 | 5/1987 | Lerman | 128/80 F X |
| 4,691,698 | 9/1987 | Bremer | 128/80 R |
| 4,727,861 | 3/1988 | Yeomans et al. | |
| 4,781,180 | 11/1988 | Solomonow | |
| 4,865,024 | 9/1989 | Hensley et al. | 128/78 X |
| 4,919,118 | 4/1990 | Morris | 128/80 H X |
| 4,934,075 | 6/1990 | Benetti et al. | 36/117 X |
| 4,934,355 | 6/1990 | Porcelli | 128/80 H |
| 4,955,149 | 9/1990 | Ottieri | 128/80 H X |

Primary Examiner—Richard J. Apley
Assistant Examiner—Linda C. Dvorak
Attorney, Agent, or Firm—Cahill, Sutton & Thomas

[57] ABSTRACT

An orthotic device for limiting limb motion at a joint has two pivotally connected members which are shaped to conform to the portions of the anatomy on opposite sides of the joint. One member has an abutment thereon engageable by an adjustable stop on the other member to limit pivotal movement between the two members. The other member is preferably formed of sheet plastic material which is formed around a mounting block which threadably receives an adjusting member for adjusting the stop.

10 Claims, 1 Drawing Sheet

U.S. Patent
June 11, 1991
5,022,390
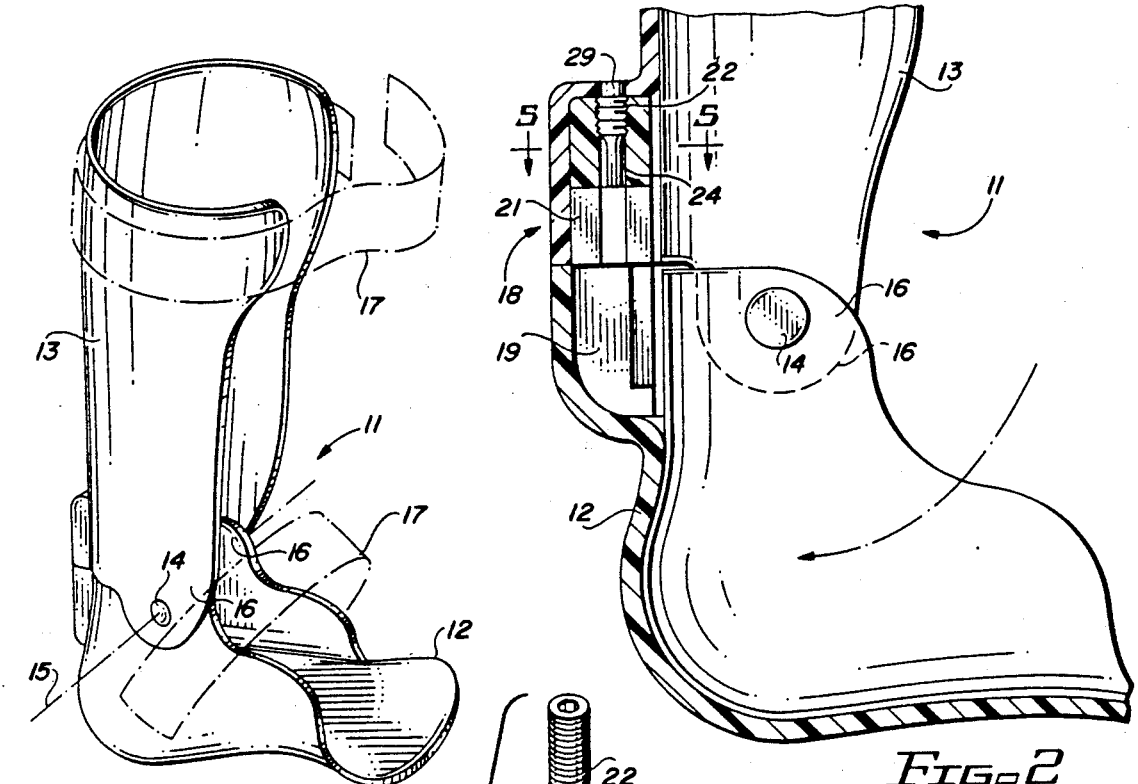
FIG. 1
FIG. 2
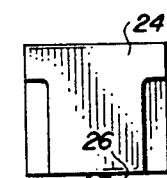
FIG. 4
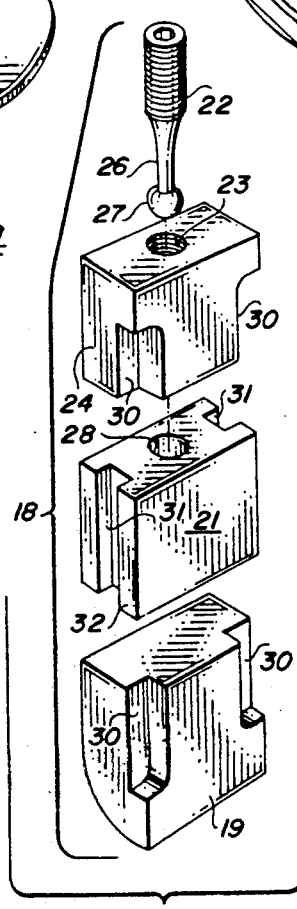
FIG. 3
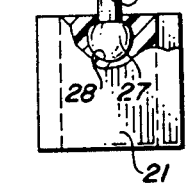
FIG. 5
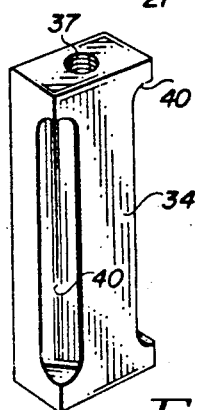
FIG. 7
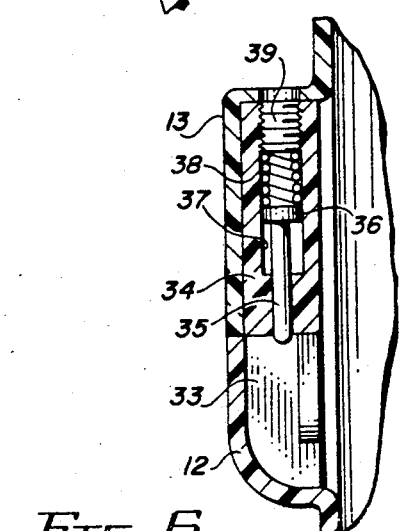
FIG. 6

ORTHOTIC DEVICE FOR LIMITING LIMB NOTION AT A JOINT

TECHNICAL FIELD

This invention relates to orthotic devices for controlling and limiting movement of a joint for a limb of the human body.

BACKGROUND ART

Orthotic devices, often called "braces", have been devised in the past for virtually every limb joint of the human body. For example, U.S. Pat. No. 2,477,591 granted Aug. 2, 1949 to E. C. Follis for "SURGICAL BRACE" discloses what can be considered a typical ankle brace. A hip joint brace is disclosed in U.S. Pat. No. 4,727,861 granted Mar. 1, 1988 to D. Yeomans et al. for "JOINT FOR ORTHOTIC DEVICE". And U.S. Pat. No. 4,781,180 granted Nov. 1, 1988 to M. Solomonow for "ORTHOTIC KNEE BRACE SYSTEM AND METHOD" discloses a representative knee brace.

Each of the orthotic devices disclosed in the aforementioned patents includes an adjustable stop mechanism for limiting pivotal movements between different components of the device. Those stop mechanisms require machined metal parts and, hence, tend to be expensive to manufacture.

DISCLOSURE OF THE INVENTION

This invention contemplates an orthotic device which is simple and inexpensive to manufacture, but which is highly reliable in its operation as well as comfortable to wear.

The device comprises two pivotally connected members which are adapted to be fastened to portions of the anatomy on opposite sides of the joint that is to be controlled. At least one and preferably both of these members are thermoformed from plastic sheet material so that their inner surfaces conform substantially to the limb or other portion of the anatomy to which they are fastened. One of these members has an abutment thereon which cooperates with an adjustable stop on the other member to limit pivotal movement between the members. Adjustment of the stop is effected by an adjusting member threadably carried in a mounting block about which the sheet material of the other member is closely formed. This securement of the mounting block preferably takes place as the other member is formed to the shape of the limb or other portion of the anatomy to which it is to be fastened. The thermoforming process employed to shape this other member causes the plastic sheet to form around and grip the mounting block thereby holding it in place.

BRIEF DESCRIPTION OF THE DRAWINGS

FIG. 1 is a perspective view of an orthotic device embodying the invention;

FIG. 2 is an enlarged, fragmentary, vertical sectional view through the advice of FIG. 1;

FIG. 3 is an enlarged exploded perspective view of a stop mechanism employed in the device;

FIG. 4 is an elevational view of a portion of the stop mechanism of FIG. 3;

FIG. 5 is a horizontal sectional view taken as indicated by line 5—5 in FIG. 2;

FIG. 6 is a vertical sectional through a modified stop mechanism;

FIG. 7 is a perspective view of a mounting block employ in the stop mechanism shown in FIG. 6.

BEST MODES FOR CARRYING OUT THE INVENTION

Referring particularly to FIGS. 1 and 2, the orthotic device, or orthosis, there illustrated is identified generally by reference numeral 11. This particular device is designed specifically to control motion of a foot about an ankle joint, neither of which limb members are shown in the drawing. It is to be understood, however, that the principles of construction of orthosis 11 and the invention embodied therein are applicable to control movement of other limbs about other joints of the human anatomy.

Basically, the orthosis 11 is comprised of two members, 12 and 13, pivotally connected at 14 for angular movement about an axis 15 which is substantially coextensive with the major horizontal axis of the wearer's ankle joint Each of the members 12 and 13 is configured to have its inner surface in conformance with that portion of the human anatomy to which it is to be secured. First member 12 is configured to closely receive and contact the surface of the heel and rear instep portion of the wearer's foot. Second member 13 is configured to closely receive and contact the wearer's lower calf. Overlapping tab regions 16 of members 12 and 13 receive rivets which provide the pivotal connection 14 between the members. Flexible straps (shown in phantom at 17) with fabric hook and loop fasteners may be employed to hold the members 12 and 13 in position on the limb.

Orthosis members 12 and 13 are preferably formed of thermoplastic sheet material such as polypropylene or a mixture of polypropylene and polyethylene. Such materials can be easily vacuum thermoformed into intricate configurations, are quite strong and are semi-flexible so they are comfortable when worn in contact with parts of the human body.

Fabricating members 12 and 13 first requires that casts be made of the wearer's limb and from these casts male molds are made in the configuration of the limbs. Warm sheets of plastic are draped over the male molds and a vacuum applied there beneath to pull the sheets over and into intimate contact with the molds. After being cooled the members 12 and 13 are trimmed to the desired peripheral configurations As with most orthotic appliances, it is desirable to limit the extent of pivotal movement of members 12 and 13. In this instance, the objective is to limit the extent to which the foot can be tilted downwardly about the ankle. This is accomplished by means of an adjustable stop mechanism, indicated generally by reference numeral 18, carried at the rear portions of adjoining sections of members 12 and 13.

The components of adjustable stop mechanism 18 of the device shown in FIGS. 1 and 2 are illustrated in greater detail in FIGS. 3, 4 and 5. Mechanism 18 comprises an abutment 19 carried by the first, or foot, member 12. Carried by the second, or calf, member 13 is an adjustable stop 21 positioned to engage abutment 19 when the members 12 and 13 have been pivotally moved the maximum desired extent. Adjustment of the position of stop 21 is effected by an adjusting screw 22 received in a threaded passage 23 through a mounting block 24.

Adjusting screw 22 is connected to adjustable stop 21 by a neck 26 having an enlargement 27 of the end thereof which is snapfitted into a recess 28 in the stop (see FIGS. 3 and 4). Turning adjusting screw into or out of mounting block 24, respectively, causes adjustable stop 21 to move toward or away from abutment 19.

Adjustable stop mechanism 18 is preferably installed in the orthosis members 12 and 13 as the latter are fabricated, i.e. as they are thermoformed. This is done by temporarily affixing the several components of stop mechanism 18 in appropriate positions on the male molds before the plastic sheets are thermoformed over these molds. In other words, the abutment is placed on the mold portion forming the upper reach of the member 12. The adjustable stop 21 and the mounting block 24 are placed on the mold for member 13 in the region near the lower rear edge of the latter member.

Abutment 19 is to be fixed in place in the first member 12 and the mounting block 24 is to be fixed in place in the second member 13. This is assured by providing corner indentations 30 in the forward corners of both the abutment 19 and the mounting block 24. When the plastic sheets forming members 12 and 13 are drawn down onto the molds and over the components of the adjustable stop mechanism 18 the plastic flows into indentations 30 locking abutment 19 and mounting block 24 firmly into their respective members.

Adjustable stop 21 preferably is provided with an elongated continuous groove 31 in each of its side faces 32. During the vacuum thermoforming process portions of the sheet plastic forming member 13 enter these grooves 31 and form rails over which stop 21 can slide in and out of member 13.

Note that placing components of adjustable stop mechanism 18 on the molds results in the surfaces of mounting block 24, stop 21 and abutment 19 being substantially flush with the inner surface regions of members 12 and 13 surrounding those components. The components of the adjustable stop mechanism thus do not interfere with placement of the wearer's limb in the orthosis 11.

Also, the construction results in the components of the adjustable stop mechanism 18 being smoothly covered by the plastic sheet material forming the members 12 and 13. The components of the stop mechanism 18 are thus not exposed to snag, tear or become entangled with the wearer's clothing.

The orthosis is completed by drilling an access hole 29 in member 13 to permit installation and manipulation of adjusting screw 22 (see FIG. 2).

FIGS. 6 and 7 illustrate a modified adjustable stop mechanism for the orthosis 11. This mechanism includes an abutment 33 mounted on member 12. A somewhat different mounting block 34 carries a pin like adjustable stop 35. Stop 35 has a piston 36 at its upper end which is positioned in an elongated chamber 37. Chamber 37 also contains a helical compression spring 38 and a set screw 39.

Turning set screw 39 adjusts the compression of spring 38 thereby altering the resistance offered to the movement of abutment 33. The spring 38 reduces the shock of abutment 33 contacting stop 35 and the spring acting through pin stop 35 assists in moving the foot upwardly during its initial motion.

Mounting block 34 is affixed to its member 13 in the same manner as mounting block 24 described above. For this purpose the mounting block 34 may be provided with corner indentations 40 (see FIG. 7).

What is claimed is:

1. An orthotic device for a limb joint, said device comprising first and second members, said first member being adapted to be attached to that portion of the anatomy to one side of the joint, said second member being formed of plastic sheet material the inner surface of which substantially conforms to that portion of the anatomy to the other side of the joint, a pivotal connection between said first and second members, said pivotal connection having an axis substantially corresponding to an axis of motion of the joint, an abutment carried by said first member, an adjustable stop carried by said second member for limiting pivotal movement between said first and second members, a mounting block carried by said second member, the plastic sheet of said second member being formed closely about said mounting block to hold said block in place, and an adjusting member threadably received in said mounting block and adapted to adjust said stop.

2. The orthotic device of claim 1 further characterized in that said adjustable stop has oppositely disposed walls, each of said stop walls having a groove therein and the sheet material for said second member is thermoformed closely about said stop walls and into said grooves to provide rails permitting sliding movement of the stop.

3. The orthotic device of claim 2 further comprising means for connecting said adjusting member to said stop.

4. The orthotic device of claim 1 further comprising a spring carried in said mounting block and providing a resilient connection between said adjusting member and said stop.

5. The orthotic device of claim 1 further characterized in that said mounting block has at least one indentation in a surface thereof engageable by the sheet material of said second member, the sheet material of said second member being thermoformed into the indentation in said mounting block for retaining said block on said second member.

6. An orthotic device for a limb joint, said device comprising first and second members, said first member being thermoformed of plastic sheet material the inner surface of which substantially conforms to that portion of the anatomy to one side of the joint, said second member being thermoformed of plastic sheet material the inner surface of which substantially conforms to that portion of the anatomy to the other side of the joint, a pivotal connection between said first and second members, said pivotal connection having an axis adapted to substantially correspond to an axis of motion of the joint, an abutment carried by said first member, said first member being thermoformed closely about said abutment to hold said abutment in place with its surface substantially flush with adjoining inner surface regions of the first member, an adjustable stop carried by said second member engageable with said abutment for limiting pivotal movement between said first member and said second member, a mounting block carried by said second member, said second member being thermoformed closely about said mounting block to hold said block in place with its inner surface substantially flush with adjoining inner surface regions of said second member, and an adjusting member threadably received in said mounting block and adapted to adjust said stop.

7. The orthotic device of claim 6 further characterized in that said adjustable stop has oppositely disposed walls, each of said stop walls having a groove therein and sheet material of said second member is thermoformed closely about said stop walls and into said grooves to provide rails permitting sliding movement of the stop.

8. The orthotic device of claim 7 further comprising means for connecting said adjusting member to said stop.

9. The orthotic device of claim 6 further comprising a spring carried in said mounting block and providing a resilient connection between said adjusting member and said stop.

10. The orthotic device of claim 6 further characterized in that said mounting block has at least one indentation in a surface thereof engageable by the sheet material of said second member, the sheet material of said second member being thermoformed into the indentation in said mounting block for retaining said block on said second member.

* * * * *

UNITED STATES PATENT AND TRADEMARK OFFICE
CERTIFICATE OF CORRECTION

PATENT NO. : 5,022,390
DATED : June 11, 1991
INVENTOR(S) : STACEY A. WHITESIDE

It is certified that error appears in the above-identified patent and that said Letters Patent is hereby corrected as shown below:

ON THE TITLE PAGE: in the title: change "NOTION" to -- MOTION --

In Col. 1, line 2, change "NOTION" to -- MOTION --

Signed and Sealed this

Twenty-fourth Day of November, 1992

Attest:

DOUGLAS B. COMER

Attesting Officer

Acting Commissioner of Patents and Trademarks